US012730101B2

(12) United States Patent
Yi et al.

(10) Patent No.: US 12,730,101 B2
(45) Date of Patent: Sep. 8, 2026

(54) SYSTEM FOR DETECTING CONTAMINATION CONDITION OF LUBRICATING GREASE OF MECHANICAL COMPONENT AND BEARING SYSTEM

(71) Applicant: Aktiebolaget SKF, Gothenburg (SE)

(72) Inventors: Xing Yi, Shanghai (CN); Defeng Lang, Delft (NL); Yu Xin Zhou, Shanghai (CN)

(73) Assignee: Aktiebolaget SKF, Gothenburg (SE)

( * ) Notice: Subject to any disclaimer, the term of this patent is extended or adjusted under 35 U.S.C. 154(b) by 309 days.

(21) Appl. No.: 18/481,410

(22) Filed: Oct. 5, 2023

(65) Prior Publication Data

US 2024/0133860 A1 Apr. 25, 2024

(30) Foreign Application Priority Data

Oct. 14, 2022 (CN) ........................ 202211261592.3

(51) Int. Cl.
*G01N 33/28* (2006.01)
*F16N 29/00* (2006.01)
*G01N 22/00* (2006.01)

(52) U.S. Cl.
CPC ......... *G01N 33/2888* (2013.01); *G01N 22/00* (2013.01); *F16C 2233/00* (2013.01); *F16N 29/00* (2013.01); *F16N 2200/00* (2013.01)

(58) Field of Classification Search
CPC ........ G01N 33/26; G01N 33/28; G01N 33/30; G01N 22/00; G01N 22/005; G01N 22/02; G01N 22/04
See application file for complete search history.

(56) References Cited

U.S. PATENT DOCUMENTS 10,378,585 B2 8/2019 Lang et al.
2005/0264302 A1* 12/2005 Mohajer ................ G01N 22/00 324/639
2013/0176038 A1* 7/2013 Wherritt ............ G01N 33/2829 324/675
2018/0038417 A1* 2/2018 Lang .................... F16C 41/008

FOREIGN PATENT DOCUMENTS

CN 102469472 B * 3/2016 ............. H04B 17/29

* cited by examiner

*Primary Examiner* — Herbert K Roberts
(74) *Attorney, Agent, or Firm* — Stinson LLP

(57) ABSTRACT

The present disclosure provides a system for detecting the contamination condition of lubricating grease of a mechanical component. The system comprises a radio frequency signal generator, a sensor, a switch assembly and a radio frequency signal analyzer. The radio frequency signal generator generates a radio frequency signal with a frequency higher than 1.0 GHz. The sensor contacts lubricating grease to be sensed in the mechanical component. The switch assembly switches between a first mode, in which a radio frequency signal is transmitted through a first transmission path, thereby providing a first feedback signal for the radio frequency signal analyzer, and a second mode in which the radio frequency signal is transmitted through a second transmission path, thereby providing a second feedback signal for the radio frequency signal analyzer. The radio frequency signal analyzer analyzes the first and second feedback signals to detect the contamination condition of lubricating grease.

22 Claims, 4 Drawing Sheets

100

200

SYSTEM FOR DETECTING CONTAMINATION CONDITION OF LUBRICATING GREASE OF MECHANICAL COMPONENT AND BEARING SYSTEM

CROSS-REFERENCE TO RELATED APPLICATION

This application claims priority to Chinese Application No. 202211261592.3, filed Oct. 14, 2022, the entirety of which is hereby incorporated by reference.

FIELD

The present disclosure relates to the field of lubrication, in particular to a system for detecting contamination condition of lubricating grease of a mechanical component and a bearing system.

BACKGROUND

Usually, lubrication management runs through the whole life cycle of equipment, so it is necessary to detect and evaluate the lubrication condition of the equipment. One of the aspects of lubrication detection and evaluation is to detect contamination condition of lubricating grease. The contamination condition of the lubricating grease will not only affect its lubricating ability, but also potentially cause damage to the equipment (such as bearings). Therefore, in many applications, it is necessary to regularly detect the lubricating grease to evaluate the contamination condition of the lubricating grease. When the contamination condition reaches an unacceptable level, an alarm signal can be sent to the lubrication system to avoid damage to the equipment or system using the lubricating grease and ensure the normal operation of the equipment or system. Therefore, higher and higher requirements are put forward for the accuracy of detection and evaluation of the lubricating grease. There is room for improvement. Therefore, an improved solution is needed to further improve the detection accuracy of contamination of the lubricating grease.

SUMMARY

In view of the above problems, according to one aspect of the present disclosure, a system for detecting contamination condition of lubricating grease of a mechanical component is provided. The system comprises a radio frequency signal generator, a sensor, a switch assembly and a radio frequency signal analyzer. The radio frequency signal generator is configured to generate a radio frequency signal with a frequency higher than 1.0 GHz; the sensor comprises a sensing assembly configured to contact lubricating grease to be sensed in the mechanical component; the switch assembly is configured to switch between a first mode and a second mode, wherein when the switch assembly is in the first mode, the radio frequency signal is transmitted via a first transmission path, thereby providing a first feedback signal for the radio frequency signal analyzer, and when the switch assembly is in the second mode, the radio frequency signal is transmitted via a second transmission path, thereby providing a second feedback signal for the radio frequency signal analyzer; the radio frequency signal analyzer is configured to perform analysis based on both the first feedback signal and the second feedback signal to detect the contamination condition of the lubricating grease.

In some embodiments, the sensing assembly is configured to contact the lubricating grease to be sensed in the mechanical component when the mechanical component is in operation.

In some embodiments, the first feedback signal comprises a first set of feedback signals corresponding to a set of carrier frequencies; the second feedback signal comprises a second set of feedback signals corresponding to the set of carrier frequencies.

In some embodiments, the radio frequency signal analyzer is further configured to: perform signal processing on the first set of feedback signals to obtain a signal-processed first set of signals; obtain a first set of amplitude values of the first set of signals; perform signal processing on the second set of feedback signals to obtain a signal-processed second set of signals; obtain a second set of amplitude values of the second set of signals; calculate a set of amplitude differences between the first set of amplitude values and the second set of amplitude values.

In some embodiments, the radio frequency signal analyzer is further configured to: determine a resonance point based on the set of amplitude differences and the set of carrier frequencies; based on the resonance point, evaluate the contamination condition of the lubricating grease.

In some embodiments, the system further comprises a controller configured to control the switch assembly to switch between the first mode and the second mode.

In some embodiments, the switch assembly comprises two single-point double-throw (SPDT) switches.

In some embodiments, the mechanical component comprises a bearing, wherein the sensor is mounted on a fixed inner ring or outer ring of the bearing, or on a seat where the outer ring is mounted, so that the sensing assembly of the sensor can contact the lubricating grease to be sensed in the bearing.

In some embodiments, the bearing comprises a fan bearing, the outer ring of the fan bearing is fixed, and the sensor is mounted between the radial three o'clock direction and the radial nine o'clock direction of the outer ring, so that the sensing assembly of the sensor faces the radial inner direction.

In addition, according to another aspect of the present disclosure, a bearing system is provided. The bearing system comprises a bearing, lubricating grease and a system for detecting the contamination condition of the lubricating grease.

Based on the above, in the system for detecting the contamination condition of lubricating grease of a mechanical component proposed by the present disclosure, by adopting a radio frequency signal obtained by amplitude modulation instead of a standard sine wave signal commonly used at present, the emitted detection signal for detecting lubricating grease contains more different amplitude information for calculating and evaluating resonator parameters (such as frequency, amplitude attenuation, etc.). The diversity of the amplitude information of the detection signal can further improve the accuracy of calculation and evaluation based on the amplitude information. In addition, a switch assembly is introduced into the system proposed in the present disclosure. By controlling the switching mode of the switch assembly to generate different signal transmission paths and by calculating the differences between the different signal transmission paths, a self-calibration process of signal transmission in each frequency carrier measurement is realized, thus eliminating the influence of signal transmission paths on calculation and evaluation. Therefore, the detection and evaluation of the lubricating grease contamination condition based on the self-calibrated signal can further improve the detection accuracy. In addition, the present disclosure adopts a solution combining a software processing method based on RF signals with a switch assembly, so that the detection accuracy can be improved without additional high-performance and expensive components. Therefore, the system of the present disclosure ensures the low cost of products while improving the detection accuracy of lubricating grease contamination.

BRIEF DESCRIPTION OF THE DRAWINGS

The system can be better understood with reference to the following description in combination with the accompanying drawings. The components in the drawings are not to scale, emphasis instead being placed upon illustrating the principles of the present disclosure. Further, in the drawings, similar or identical reference numerals represent similar or identical elements.

DETAILED DESCRIPTION

Figure 1:
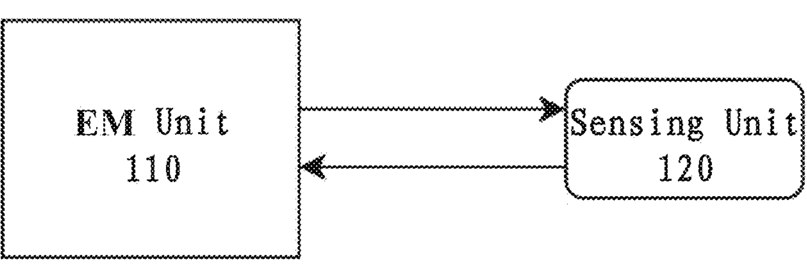
FIG. 1 schematically illustrates a schematic diagram of a system 100 for detecting and evaluating the contamination condition of lubricating grease according to some embodiments of the present disclosure.

It should be understood that the following description of the embodiments is given for illustrative purposes only, and is not restrictive. The exemplary division of functional blocks, modules or units shown in the drawings should not be interpreted to mean that these functional blocks, modules or units must be implemented as physically separate units. The functional blocks, modules or units shown or described may be implemented as individual units, circuits, chips, functions, modules or circuit elements. One or more functional blocks or units may also be implemented in a common circuit, chip, circuit element or unit.

As shown in the present application and claims, unless the context clearly suggests an exception, words “a”, “an” and/or “the” do not specifically refer to the singular, but may also comprise the plural. Generally speaking, terms “comprising” and “including” only imply the inclusion of clearly identified steps and elements, and these steps and elements do not constitute an exclusive list, and a method or device may also contain other steps or elements.

Although the present application makes various references to some modules in the system according to the embodiments of the present application, any number of different modules can be used and run on the user terminal and/or the server. The modules are merely illustrative, and different aspects of the system and method may use different modules.

Flowcharts are used in the present application to explain the operations performed by the system according to the embodiments of the application. It should be understood that the preceding or following operations are not necessarily performed accurately in order. On the contrary, various steps can be processed in reverse order or at the same time as required. Meanwhile, other operations can be added to these processes, or one or more steps can be removed from these processes.

FIG. 1 shows a schematic diagram of a system 100 for detecting and evaluating the contamination condition of lubricating grease according to some embodiments of the present disclosure. Referring to FIG. 1, the system 100 comprises, for example, an electromagnetic (EM) unit 110 and a sensing unit 120. Signal transmission between the electromagnetic unit 110 and the sensing unit 120 can be conducted through wired or wireless means.

In some examples, the lubricating grease is lubricating grease in a mechanical component, the mechanical component comprising but not limited to bearings, gears, turbines and other mechanical components that need lubricating grease. The contamination condition of the lubricating grease can be directly detected when the mechanical component is stationary, or the lubricating grease can be taken out for detection of the contamination condition when the mechanical component is stationary, or the contamination condition of the lubricating grease in the mechanical component can be detected when the mechanical component is running. For example, for some mechanical components that are inconvenient to achieve stationary at any time or difficult to get close to, such as large bearings, the present disclosure can be used to detect the contamination condition of lubricating grease therein when they are running, so as to give timely warning to replace the lubricating grease when the contamination condition reaches a threshold, wherein the contamination condition comprises the level of unacceptable water or particulate pollutants contained in the lubricating grease.

In some examples, the electromagnetic unit 110 may generate a high-frequency radio frequency (RF) signal and send the generated RF signal to the sensing unit 120. The RF signal is a modulated signal obtained by modulating a standard sine wave signal. The electromagnetic unit 110 can operate in a very wide frequency range, for example, its maximum operating frequency range can be 1 GHz to 100 GHz.

In some examples, the sensing unit 120 receives an RF signal transmitted by the electromagnetic unit 110 and transmits a feedback signal to the electromagnetic unit 110. The parameters of the feedback signal will change with the contamination level of grease. For example, the sensing unit 120 may comprise a sensor, which may be in contact with the grease through a sensing assembly thereon, so as to sense the contamination condition of the grease. The presence of grease will affect the parameters of the feedback signal.

After receiving the feedback signal from the sensor 120, the electromagnetic unit 110 will perform analysis on the feedback signal. In some examples, the contamination level of the grease can be analyzed by detecting the change between the RF signal generated by the electromagnetic unit 110 and the feedback signal received from the sensor.

Considering that RF signal is very sensitive to small values of capacitance and inductance, it is not easy to obtain stable RF signal in the process of signal transmission compared with low frequency signal. In application, the differences of designed and parasitic capacitance/inductance exist widely in discrete elements, cables and RF IC, and these parameters themselves will change with the environmental parameters (temperature, humidity, etc.). The differences between all the above elements and the elements themselves can lead to the deterioration of the amplitude stability of the RF signal transmitted to the sensor. It is usually necessary to adopt high-performance elements to reduce the above affection.

Figure 2:
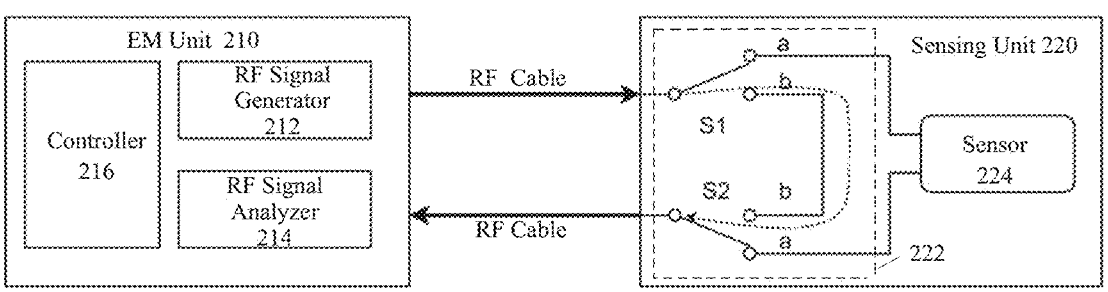
FIG. 2 schematically illustrates a module diagram of a system 200 for detecting and evaluating the contamination condition of lubricating grease according to some embodiments of the present disclosure.

Based on the above, the present disclosure proposes a further improvement solution on the basis of the system 100 of the embodiment of the present disclosure shown in FIG. 1. FIG. 2 illustrates a module diagram of a system 200 for detecting and evaluating the contamination level of lubricating grease according to an embodiment of the present disclosure, so as to explain its working principle.

The system 200 comprises an electromagnetic (EM) unit 210 and a sensing unit 220. Generally, the electromagnetic unit 210 sends a signal to the sensing unit 220, receives a feedback signal from the sensing unit 220, and detects and evaluates the contamination condition in lubricating grease based on the feedback signal.

Figure 3:
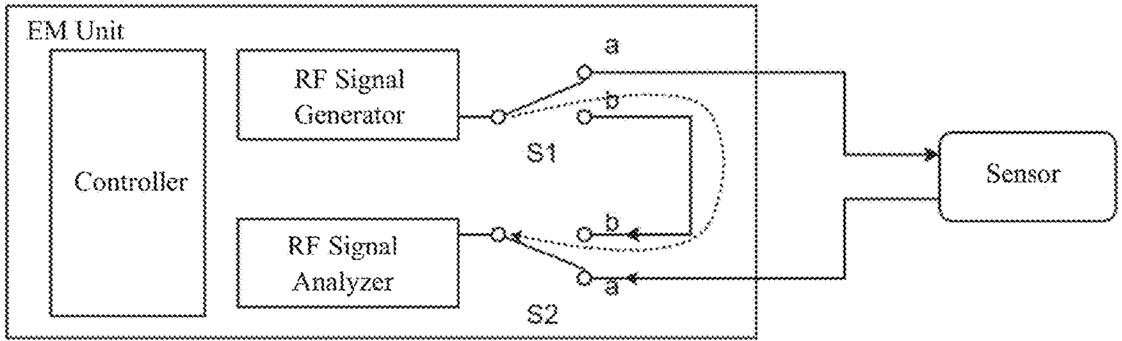
FIG. 3 schematically illustrates another module diagram of a system 200 for detecting and evaluating the contamination condition of lubricating grease according to some embodiments of the present disclosure.

In some examples, the electromagnetic unit 210 may comprise a radio frequency (RF) signal generator 212, a radio frequency (RF) signal analyzer 214, and a controller 216. The sensing unit 220 may comprise a switch assembly 222 and a sensor 224. The switch assembly 222 may be composed of two single-point double-throw switches S1 and S2, for example. The sensor 224 may be, for example, a ring resonator RR. The sensor 224 comprises a sensing assembly configured to contact the lubricating grease to be sensed. In the exemplary schematic diagram of FIG. 2, the electromagnetic unit 210 may further comprise a controller 216. It can be understood that the layout of the system 200 shown in FIG. 2 is only for the purpose of explaining the principles of the system for realizing the technical solution of the present disclosure, and is not a restriction on the physical location of each module or assembly in each unit. In other examples, the RF signal generator 212, the RF signal analyzer 214 and the controller 216 can all be arranged independently, or any two or more of them can be integrated in a functional unit or functional module. In other examples, the switch assembly may be arranged independently of the sensing unit 220, or may be arranged in the electromagnetic unit 210. In addition, in the exemplary schematic diagram of FIG. 2, an RF cable may be adopted as the signal transmission medium between the electromagnetic unit 210 and the sensing unit 220. It can be understood that in some other examples, a digital control cable may also be adopted as the signal transmission medium between the electromagnetic unit 210 and the sensing unit 220. In addition, the signal transmission medium between the electromagnetic unit 210 and the sensing unit 220 can also be air, that is to say, there is no need for any wired connection between the electromagnetic unit 210 and the sensing unit 220. It can be understood that a combination solution of any arrangement of functional units, modules, components, elements, etc. as described above with any one or more of the signal transmission media are within the scope of the present disclosure. For example, as an example of a combination solution, FIG. 3 shows a schematic diagram of the system in a case where there is no RF cable or the RF cable is very short, wherein the switch assembly (S1, S2) is arranged in the electromagnetic unit. It can be understood that there are also many modular schematic diagrams of systems of above-mentioned various combination solutions, which are all applicable to the specific process of the operation of a system introduced below in the present disclosure. The various modular schematic diagrams of the systems are not exhaustive here.

For the sake of brevity and clarity, the solution proposed by the present disclosure will be further described in detail below only for the system schematic diagram illustrated in FIG. 2.

Figure 4:
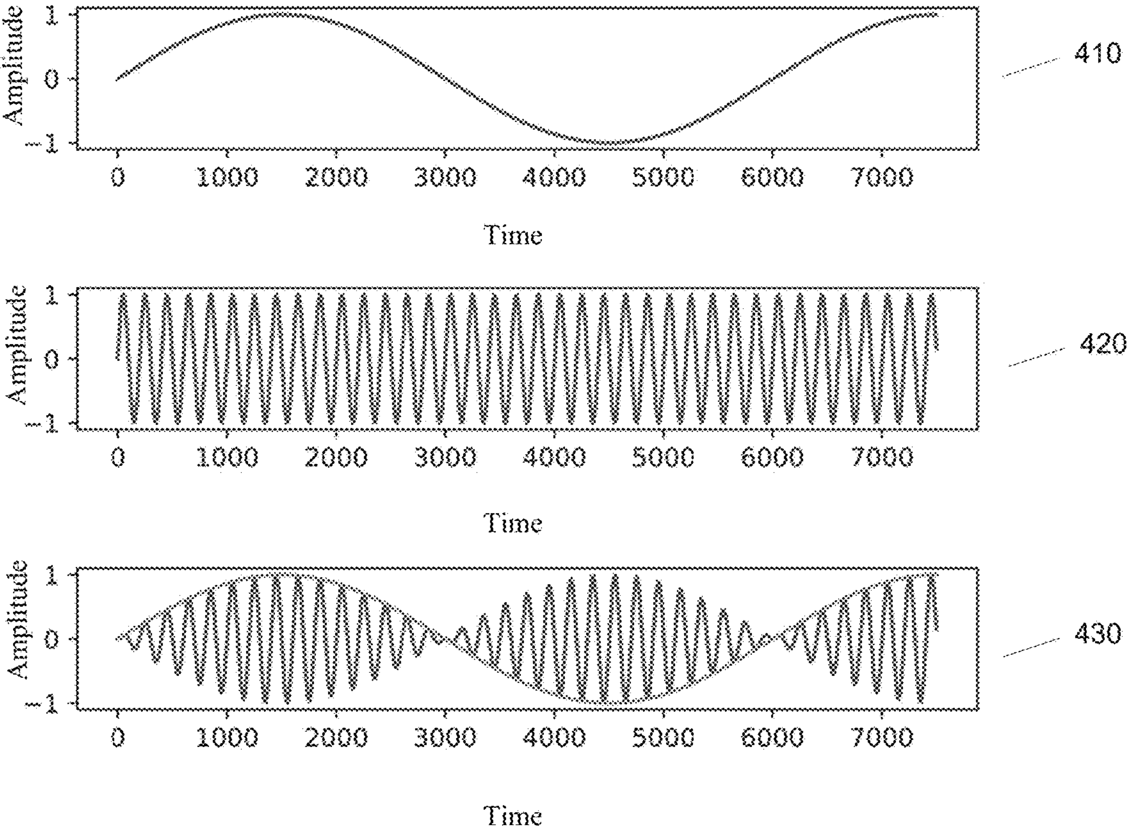
FIG. 4 schematically illustrates various waveform diagrams in the process of modulating a carrier signal to generate a modulated RF signal according to some embodiments of the present disclosure.

Referring to FIG. 2, the RF signal generator 212 may generate an RF signal, which is a signal obtained by modulating a standard sinusoidal signal (i.e., a carrier signal). In some examples, the carrier signal can be amplitude-modulated using an amplitude modulation scheme to generate the RF signal. In this example, the RF signal is an amplitude-modulated signal. FIG. 4 shows exemplary waveforms in the above-mentioned process of modulating a carrier signal to generate an RF signal. Signal waveform 410 shows the amplitude modulation signal used for amplitude modulation of the carrier signal. Signal waveform 420 shows the carrier signal (for example, standard sine wave), and signal waveform 430 shows the amplitude-modulated signal generated (i.e., the generated RF signal) after amplitude modulation of the carrier signal by using the modulation signal. Compared with the currently commonly used solution in which standard sine wave signal serves as the output signal of the electromagnetic unit (equivalent to only sending the carrier signal), the system of the present disclosure generates an amplitude-modulated signal (that is, an RF signal) through an RF signal generator, so that the signal output from the electromagnetic unit in the system of the present disclosure contains more different amplitude information. For example, compared with the case in which waveform 420 only has two amplitude values 1 and −1, waveform 430 has more amplitude values. Therefore, the RF signal designed by the present disclosure carries more amplitude information. This signal design containing more amplitude information allows to improve the accuracy of subsequent calculation and evaluation methods based on amplitude information.

The above only gives an example of a modulation signal whose waveform is a sine wave. It should be understood that modulation signals with other waveforms can also be selected according to actual needs, for example, triangular waveforms, sawtooth waveforms, other waveforms or combinations of the above different waveforms can also be selected. It should be understood that the embodiments of the present disclosure are not limited by the specific waveform of the modulation signal.

Returning to FIG. 2, the switch assembly 222 in the example in FIG. 2 comprises a first single-point double-throw switch S1 and a second single-point double-throw switch S2. The first single-point double-throw switch S1 comprises a first fixed terminal and two first moving terminals; the second single-point double-throw switch S2 comprises a second fixed terminal and two second moving terminals. In order to represent the signal transmission paths more clearly and intuitively, the respective two moving terminals of the two switches S1 and S2 in the figure are identified by symbols a and b. The switching of the two switches S1 and S2 can be controlled by the controller 216. In addition, the controller 216 can also perform logical control on the cooperation of various parts of the system 200. For example, the controller may further control the RF signal generator 212, the RF signal analyzer and their logic in cooperation with the switch assembly 222. It can be understood that the RF signal generator 212, the RF signal analyzer and the controller 216 can be implemented in hardware, implemented in software or a combination of the two.

In the example of FIG. 2, the RF signal generated by the RF signal generator 212 is transmitted through an RF cable, for example. By switching the switch assembly 222 between two modes, the RF signal can have two transmission paths. One of the transmission paths is a transmission path that does not pass through the sensor (i.e., does not pass through the ring resonator RR). For example, the RF signal generated from the RF signal generator 212 is transmitted to the RF signal analyzer via a forward RF cable, the switch S1 and the switch S2, and then via a backward RF cable. The other transmission path is a transmission path passing through the ring resonator RR (i.e., pass through the ring resonator RR). For example, the RF signal generated from the RF signal generator 212 is transmitted to the RF signal analyzer via the forward RF cable, the switch S1, the ring resonator RR and the switch S2, and then via the backward RF cable. Thus, the RF signal analyzer 214 receives signals fed back through two different transmission paths and processes and analyzes them, so that the contamination condition of the lubricating grease can be analyzed.

Figure 5:
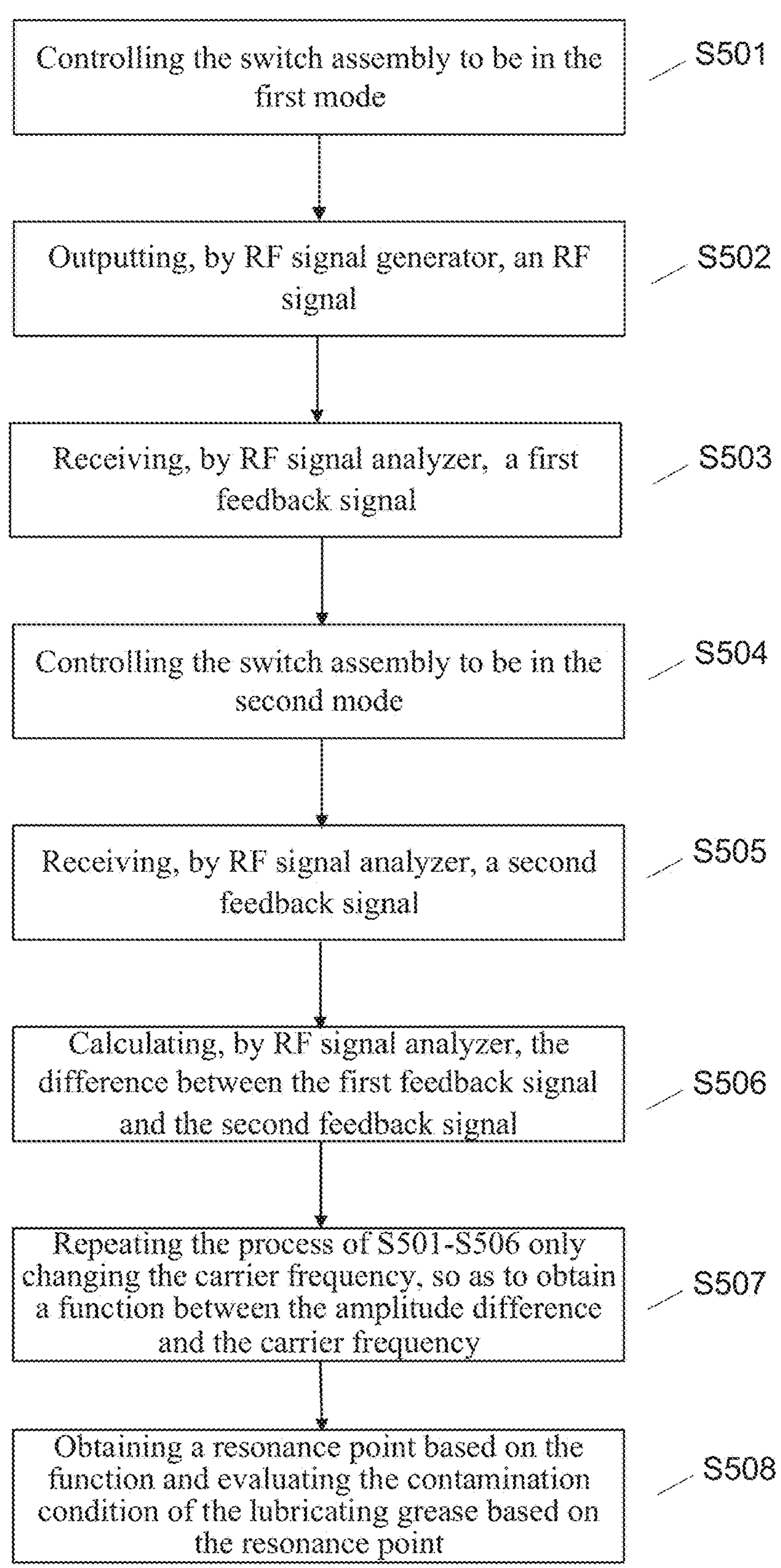
FIG. 5 schematically illustrates a work flow chart suitable for the system shown in FIGS. 2 and 3.

FIG. 5 shows a work flow chart of a system with the illustrated modules of FIGS. 2 and 3. For the sake of conciseness, the detection and evaluation process adopted by the system of the present disclosure will be described in detail below in combination with the system schematic diagram of FIG. 2 and the schematic flow chart of FIG. 5.

The key to the accurate detection and evaluation process of the contamination condition of lubricating grease in the present disclosure is to accurately detect the amplitude attenuation of the signal fed back by the sensor (that is, the ring resonator RR) to which the target lubricating grease is attached. The detection process is as follows.

At S501, the controller 216 controls the switch assembly 222 to be in the first mode. In this first mode, the fixed terminals of switches S1 and S2 are connected to their respective moving terminals b (that is, switches S1 and S2 are set at position b). In this first mode of the switch assembly, the transmission path of the RF signal is a transmission path that does not pass through the ring resonator RR, wherein the transmission path in the sensing unit portion is shown by the dashed arrow in FIG. 2.

At S502, the RF signal generator 212 outputs an RF signal, which is an amplitude-modulated signal, the waveform of which being the same as the signal waveform 430 in FIG. 4, for example. The general expression of this RF signal can be described by the following equation (1):

$$y_{source}(t)=A_m \sin(2\pi f_m t)\times\sin(2\pi f_s t) \quad \text{Equation (1)}$$

wherein, $A_m \sin(2\pi f_m t)$ is the modulation signal, which can be expressed as $y_m(t)$ for the convenience of the following description, that is, $y_m(t)=A_m \sin(2\pi f_m t)$, wherein $A_m$ and $f_m$ represent the amplitude and frequency of the modulation signal. In addition, in equation (1), $f_s$ represents the carrier frequency of the carrier signal. The range of the carrier frequency $f_s$ depends on the type of the lubricating grease. In some examples, the value of $f_s$ can range from 2.5 GHz to 3.5 GHz. In some examples, in one detection process, the value of the carrier frequency can be increased from 2.5 GHz to 3.5 GHz with an increment of 10 MHz, so that a total of 100 carrier frequency points can be included. For example, from $f_{s1}$=2.5 GHz, $f_{s2}$=2.6 GHz, . . . $f_{s100}$=3.5 GHz, 100 carrier frequency points can be included. In the same detection process, for different carrier frequency values, the values of $A_m$ and $f_m$ remain unchanged. For example, the parameter values of $A_m$ and $f_m$ can be set to $A_m$=1 and f=10 MHz.

It can be understood that the embodiments of the present disclosure are not limited by specific numerical values of signal parameters. In practical application, the required signal parameter values, such as the amplitude value and the frequency value of the modulation signal as well as the frequency value of the carrier frequency, can also be determined according to actual needs and actual application scenarios. It should be understood that the embodiments of the present disclosure are not limited by the value range of the carrier frequency and the number of the carrier frequency points. In practical application, the value range of the carrier frequency and the number of the carrier frequency points can be determined according to actual needs and actual application scenarios.

For the sake of clear explanation in principle in the following text, in an example where the carrier frequency is $f_{s1}$, for example, the RF signal generated by the RF signal generator 212 is expressed as the following equation (2).

$$y_{source1}(t)=A_m \sin(2\pi f_m t)\times\sin(2\pi f_{s1} t) \quad \text{Equation (2)}$$

At S503, the RF signal analyzer 214 receives a first feedback signal provided via the first transmission path, that is, the first feedback signal is a signal provided to the RF signal analyzer 214 that is obtained from an RF signal transmitting via the RF cable and the switch assembly. The RF signal analyzer 214 performs signal processing on the received first feedback signal. The signal processing can comprise demodulation and analog-to-digital conversion, which are not in a certain order; or the signal processing may be or comprise other possible processing. Through signal processing, the modulation signal (such as the amplitude modulation signal) can be calculated. It should be understood that a variety of existing signal demodulation solutions can be used for demodulation, including but not limited to digital solutions such as digital down converters and analog solutions such as power detection diodes. Because of the transmission, the amplitude modulation signal calculated by demodulating the first feedback signal is different from the amplitude modulation signal used in the modulation process. For convenience of understanding, the amplitude modulation signal calculated by demodulating the first feedback signal is expressed as the following equation (3):

$$y_{m1}(t)=A_{m1} \sin(2\pi f_m t) \quad \text{Equation (3)}$$

In some examples, the calculated amplitude modulation signal can be further digitized. For example, $y_{m1}(t)$ of equation (3) can be converted into a digital sequence as shown in the following equation (4) by an analog-to-digital converter:

$$y_{m1}(n) = A_{m1}\sin\left(\frac{2\pi f_m^n}{F_s}\right) \quad \text{Equation (4)}$$

wherein $F_s$ is the sampling rate of the signal, and its value is constant.

The RF signal analyzer 214 can calculate or evaluate the amplitude value $A_{m1}$ of the digital sequence based on the calculated amplitude modulation signal $y_{m1}(n)$. Because the fundamental frequencies $f_m$ of $y_{m1}(n)$ and $y_{m1}(t)$ are the same, the value of $A_{m1}$ can be obtained by digital signal processing method. For example, $y_{m1}(n)$ is first by a window function to reduce spectrum leakage and aliasing, and then DFT (Digital Fourier Transform) may be performed, and then the value of the amplitude of the signal corresponding to the frequency point of $f_m$ is equal to the value of $A_{m1}$. It should be understood that the above method of obtaining the amplitude value $A_{m1}$ is illustrated only by way of example. Other common methods in the field of signal processing can all be used to evaluate the value of $A_{m1}$, for example, including but not limited to power spectrum estimation, maximum likelihood estimation and other methods. Through the above signal processing methods (such as Digital Fourier Transform) and/or other further signal processing methods (such as curve fitting, etc.), noise interference can be reduced and detection accuracy can be greatly improved.

At S504, the controller 216 controls the switch assembly 222 to be in the second mode. In this second mode, the fixed terminals of the switches S1 and S2 are connected to their respective moving terminals a (that is, switches S1 and S2 are set at position a). Meanwhile, the RF signal output by the RF signal generator 212 remains consistent with the RF signal output at S502.

In this second mode of the switch assembly, the transmission path of the RF signal becomes the transmission path through the sensor 224 (including the ring resonator RR, for example). As mentioned above, the ring resonator can sense the lubricating grease attached to it, so the signal output through the ring resonator carries information related to the contamination level of the lubricating grease.

At S505, the RF signal analyzer 214 receives a second feedback signal provided via the second transmission path, that is, the second feedback signal is a signal provided to the RF signal analyzer 214 via the RF cable, the switch assembly and the RR ring resonator. The RF signal analyzer 214 performs signal processing on the received second feedback signal. Adopting a signal processing method similar to that described above in connection with S503, an amplitude modulation signal can be calculated, and the analog amplitude modulation signal can be further converted into a digital amplitude modulation signal. In order to save space, they are not repeated here. For example, the digital amplitude modulation signal demodulated based on the second feedback signal can be expressed as shown in the following equation (5):

$$y_{m1\_grease}(n) = A_{m1\_grease}\sin\left(\frac{2\pi f_m^n}{F_s}\right) \quad \text{Equation (5)}$$

Similarly, adopting the same method as described in S503, the RF signal analyzer 214 can calculate or evaluate the amplitude value $A_{m1\_grease}$ based on the calculated amplitude modulation signal $y_{m1\_grease}(n)$.

At S506, the RF signal analyzer 214 calculates the difference between the two feedback signals received via the two transmission paths. For example, the RF signal analyzer 214 calculates the amplitude difference between the two received feedback signals provided via the two transmission paths. For an RF signal generated based on a carrier signal with a carrier frequency of $f_{s1}$, the amplitude difference is shown in the following equation (6):

$$A_{difference} = A_{m1\_grease} - A_{m1} \quad \text{Equation (6)}$$

Figure 6:
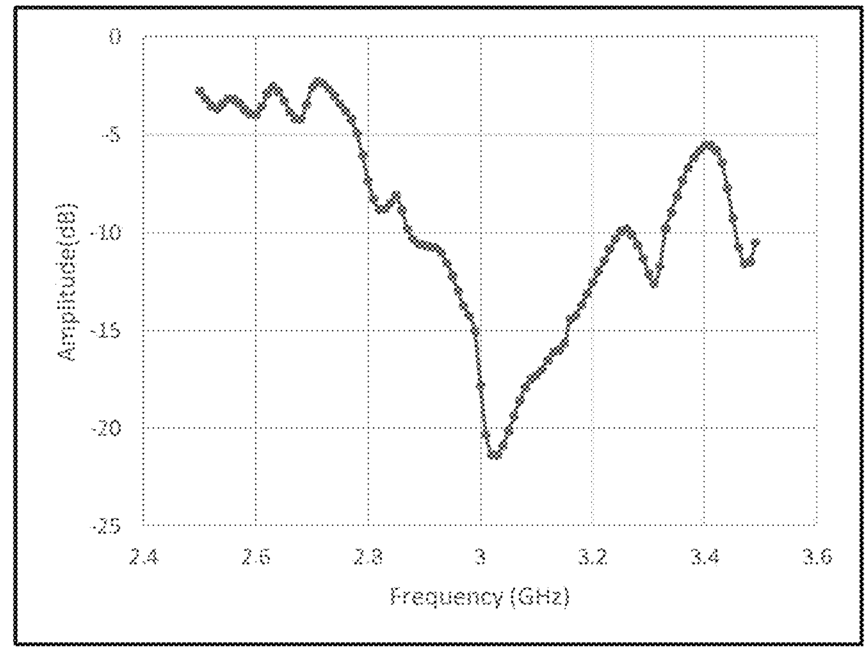
FIG. 6 schematically illustrates a graph of amplitude attenuation of lubricating grease.

At S507, the carrier frequency is changed while other parameters of the RF signal generator (such as the amplitude and frequency of the modulation signal) are kept unchanged, and then the process of S501-506 is repeated. For example, in the example where the carrier frequency ranges from 2.5 GHz to 3.5 GHz and comprises 100 carrier frequency points, the carrier frequency can be changed to $f_{s2}$ while keeping the amplitude and frequency of the modulation signal unchanged, and the process of S501-506 is repeated. And so on until the carrier frequency is changed to $f_{s100}$ while keeping the amplitude and frequency of the modulation signal unchanged, and the process of S501-506 is repeated. Thereby, a set of amplitude differences can be obtained, for example, 100 amplitude differences corresponding to 100 carrier frequency points. Therefore, a function of the amplitude difference and the carrier frequency, such as $A_{difference}(f_s)$, can be obtained. For a more intuitive description, FIG. 6 shows a curve form about the function of the amplitude difference and the carrier frequency.

At 508, based on this function, a resonance point can be obtained. For example, in this function curve, the point at the trough of the wave is the resonance point. This resonance point corresponds to the measured resonance point of the ring resonator. It can be seen from the figure that the coordinate values of the resonance point correspond to the frequency value and the amplitude value respectively. In the example shown in FIG. 6, the coordinates of the resonance point are 3.03 GHz, −23.03 dB. Because the parameter information of the resonance point (that is, the frequency and amplitude information of the resonance point) is related to the contamination condition of lubricating grease measured by the ring resonator. Therefore, based on the parameter information contained in the resonance point, the signal analyzer 214 can detect and evaluate the contamination condition of the lubricating grease. For example, the contamination condition of the lubricating grease can comprise the pollutants in the lubricating grease and the contamination level.

In some examples, for example, reference values about resonance points or a lookup table corresponding to the reference values can be stored in the signal analyzer in advance, or a reference curve corresponding to the reference values can be stored. The reference values may be obtained by measuring reference samples of the same lubricating grease in a condition without contamination. The reference values of the resonance points (resonance frequencies and resonance amplitudes) may characterize the contamination parameters of the lubricating grease (for example, pollutant type and contamination level). By comparing the measured parameters of the resonance points with the stored parameters of the reference resonance points, the signal analyzer 214 can estimate the contamination condition of the lubricating grease.

In some examples, a threshold of contamination level can be set, and when the contamination level evaluated by the signal analyzer exceeds the threshold, an alarm can be given to make the whole lubrication system take corresponding actions automatically, or to remind maintenance personnel to make corresponding decisions and take relevant optimization actions according to the alarm.

It should be understood that the present disclosure as above only gives an example that the sensor comprises a ring resonator RR, but different resonators can be adopted according to actual needs. For example, the sensor of the present disclosure may also comprise a bow-tie resonator, a split-ring resonator or a complementary split-ring resonator.

Based on the above disclosure, in the system for detecting the contamination condition of lubricating grease proposed by the present disclosure, by adopting a amplitude-modulated radio frequency signal instead of the standard sine wave signal commonly used at present, the detection signal emitted by the electromagnetic unit for detecting the lubricating grease comprises more different amplitude information for calculating and evaluating resonator parameters (such as frequency, amplitude attenuation, etc.). The diversity of the amplitude information of the detection signal can further improve the accuracy of calculation and evaluation based on the amplitude information. In addition, a switch assembly is introduced into the system proposed in the present disclosure, and by controlling the switching mode of the switch assembly to generate different signal transmission paths and by calculating the differences between different signal transmission paths, a self-calibration process of signal transmission in each frequency carrier measurement may be realized, so as to eliminate the influence of the signal transmission paths on calculation and evaluation. Therefore, the detection and evaluation of the lubricating grease contamination condition based on the self-calibrated signal can further improve the detection accuracy. In addition, the present disclosure adopts a solution combining a software processing method based on RF signals with a switch assembly, so that the detection accuracy can be improved without additional high-performance and expensive components. Therefore, the system of the present disclosure ensures the low cost of products while improving the detection accuracy of lubricating grease contamination.

In some embodiments, the sensor is mounted on the fixed inner ring or outer ring of the bearing, or on the seat where the outer ring is mounted, so that the sensing assembly of the sensor can contact the lubricating grease to be sensed in the bearing. The sensor is arranged at an appropriate position of the fixed inner ring or the fixed outer ring of the bearing, this appropriate position being for example a position in the bearing where lubricating grease is easy to deposit, such as arranged in the radial six o'clock direction of the fixed outer ring, and so that the sensing assembly of the sensor faces the radial inner direction. The sensor is used to measure the contamination condition of lubricating grease existing in the bearing. The contamination condition comprises, for example, the level of water pollutants and the level of metal particle pollutants. The presence of water in lubricating grease adversely affects its lubricating ability and may lead to corrosion in bearing. The presence of metal particles may significantly reduce the fatigue life of the rolling contact surface of the bearing. Alternatively, the sensor is mounted on the seat where the outer ring of bearing is mounted, and the sensing assembly on the sensor is arranged on a flat surface facing the radially inner side, which flat surface slightly extends, on one axial side, into the cavity between the bearing rings. During the operation of the bearing, centrifugal force acts on the lubricating grease existing on the rotating inner ring, so that the lubricating grease is thrown towards the outer ring. Therefore, some lubricating grease will be thrown out and onto the sensing assembly of the sensor, so that the contamination condition of lubricating grease in the bearing can be detected.

In some embodiments, the bearing is a fan bearing, and the outer ring of the fan bearing is fixed. The sensor is mounted between the radial three o'clock direction and the nine o'clock direction, preferably mounted on the radial six o'clock direction of the fixed outer ring, and so that the sensing assembly of the sensor faces the radial inner direction. Because the lubricating grease in the fan bearing is easy to deposit there, mounting the sensor at this position can make the sensing assembly of the sensor more easily contact the lubricating grease in the fan bearing.

It should be understood that both the RF signal analyzer and the controller in the present disclosure may comprise a memory storing computer-executable instructions/codes/logic and a processor. The processor may be a microprocessor, an application specific integrated circuit (ASIC), a system-on-a-chip (SoC), a computing device, etc. Any one or more of the processors, memories or systems described herein comprise computer-executable instructions that can be compiled or interpreted from computer programs created using various programming languages and/or technologies. In general, a processor, such as a microprocessor, receives and executes instructions, for example, from a memory, a computer-readable medium, and the like. A processor comprises a non-transitory computer-readable storage medium capable of executing instructions of a software program. The computer-readable medium may be, but is not limited to, an electronic storage device, a magnetic storage device, an optical storage device, an electromagnetic storage device, a semiconductor storage device or any suitable combination thereof.

The description of the embodiments has been presented for purposes of illustration and description. Suitable modifications and variations of the embodiments can be carried out in view of the above description or can be obtained by practical methods. For example, unless otherwise indicated, one or more of the described methods may be performed by a combination of suitable devices and/or systems. The methods may be performed by executing stored instructions with one or more logic devices (e.g., processors) in combination with one or more additional hardware elements (such as storage devices, memories, circuits, hardware network interfaces, etc.). The method and associated action may also be performed in parallel and/or simultaneously in various orders other than those described in the present disclosure. The system is exemplary in nature and may comprise additional elements and/or omit elements. The subject matter of the present disclosure comprises all novel and non-obvious combinations of various disclosed methods and system configurations and other features, functions and/or properties.

As used in the present disclosure, an element or step recited in the singular and preceded by the word "a/an" should be understood as not excluding a plurality of said elements or steps unless such exclusion is indicated. Furthermore, references to "one embodiment" or "one example" of the present disclosure are not intended to be interpreted as excluding the existence of other embodiments that also incorporate the listed features. The present disclosure has been described above with reference to specific embodiments. However, those skilled in the art will understand that various modifications and changes can be made thereto without departing from the broader spirit and scope of the present disclosure as set forth in the appended claims.

What is claimed is:

1. A system for detecting contamination condition of lubricating grease of a mechanical component, the system comprising:

a radio frequency signal generator configured to generate a radio frequency signal with a frequency higher than 1.0 GHZ;

a sensor comprising a sensing assembly configured to contact lubricating grease to be sensed in the mechanical component;

a switch assembly configured to switch between a first mode and a second mode; and a radio frequency signal analyzer;

wherein when the switch assembly is in the first mode, the radio frequency signal is transmitted via a first transmission path, thereby providing a first feedback signal for the radio frequency signal analyzer, and when the switch assembly is in the second mode, the radio frequency signal is transmitted via a second transmission path, thereby providing a second feedback signal for the radio frequency signal analyzer, the second transmission path including the sensing assembly, the first transmission path being the same as the second transmission path except the first transmission path comprises a short instead of the sensing assembly, the first feedback signal provided by the first transmission path being representative of the second transmission path without the sensing assembly; and wherein the radio frequency signal analyzer is configured to perform an analysis based on both the first feedback signal and the second feedback signal to detect the contamination condition of the lubricating grease.

2. The system according to claim 1, wherein the sensing assembly is configured to contact the lubricating grease to be sensed in the mechanical component when the mechanical component is in operation.

3. The system according to claim 1, wherein:

the first feedback signal comprises a first set of feedback signals corresponding to a set of carrier frequencies; and the second feedback signal comprises a second set of feedback signals corresponding to the set of carrier frequencies.

4. The system according to claim 3, wherein the radio frequency signal analyzer is further configured to:

perform signal processing on the first set of feedback signals to obtain a signal-processed first set of signals;

obtain a first set of amplitude values of the first set of signals;

perform signal processing on the second set of feedback signals to obtain a signal-processed second set of signals;

obtain a second set of amplitude values of the second set of signals; and calculate a set of amplitude differences between the first set of amplitude values and the second set of amplitude values.

5. The system according to claim 4, wherein the radio frequency signal analyzer is further configured to:

determine a resonance point based on the set of amplitude differences and the set of carrier frequencies; and evaluate the contamination condition of the lubricating grease based on the resonance point.

6. The system according to claim 1, wherein the system further comprises a controller configured to control the switch assembly to switch between the first mode and the second mode.

7. The system according to claim 1, wherein the switch assembly comprises two single-point double-throw (SPDT) switches.

8. The system according to claim 1, wherein the mechanical component comprises a bearing, wherein the sensor is mounted on a fixed inner ring or outer ring of the bearing, or on a seat where the outer ring is mounted, so that the sensing assembly of the sensor can contact the lubricating grease to be sensed in the bearing.

9. The system according to claim 8, wherein the bearing comprises a fan bearing, the outer ring of the fan bearing is fixed, and the sensor is mounted between the radial three o'clock direction and the radial nine o'clock direction of the outer ring, so that the sensing assembly of the sensor faces the radial inner direction.

10. The system according to claim 2, wherein:

the first feedback signal comprises a first set of feedback signals corresponding to a set of carrier frequencies; and the second feedback signal comprises a second set of feedback signals corresponding to the set of carrier frequencies.

11. The system according to claim 10, wherein the radio frequency signal analyzer is further configured to:

perform signal processing on the first set of feedback signals to obtain a signal-processed first set of signals;

obtain a first set of amplitude values of the first set of signals;

perform signal processing on the second set of feedback signals to obtain a signal-processed second set of signals;

obtain a second set of amplitude values of the second set of signals; and calculate a set of amplitude differences between the first set of amplitude values and the second set of amplitude values.

12. The system according to claim 11, wherein the radio frequency signal analyzer is further configured to:

determine a resonance point based on the set of amplitude differences and the set of carrier frequencies; and evaluate the contamination condition of the lubricating grease based on the resonance point.

13. The system according to claim 12, wherein the system further comprises a controller configured to control the switch assembly to switch between the first mode and the second mode.

14. The system according to claim 13, wherein the switch assembly comprises two single-point double-throw (SPDT) switches.

15. The system according to claim 14, wherein the mechanical component comprises a bearing, wherein the sensor is mounted on a fixed inner ring or outer ring of the bearing, or on a seat where the outer ring is mounted, so that the sensing assembly of the sensor can contact the lubricating grease to be sensed in the bearing.

16. The system according to claim 15, wherein the bearing comprises a fan bearing, the outer ring of the fan bearing is fixed, and the sensor is mounted between the radial three o'clock direction and the radial nine o'clock direction of the outer ring, so that the sensing assembly of the sensor faces the radial inner direction.

17. A bearing system comprising a bearing, lubricating grease and the system according to claim 16.

18. A bearing system comprising a bearing, lubricating grease and the system according to claim 1.

19. The bearing system of claim 1, wherein the radio frequency signal analyzer is configured to calibrate the second feedback signal to reduce an influence of the second transmission path on the second feedback signal.

20. The bearing system of claim 19, wherein the radio frequency signal analyzer is configured to calculate differences between the first and second feedback signals to calibrate the second feedback signal.

21. The bearing system of claim 1, wherein the radio frequency signal generated by the radio frequency signal generator is a modulated radio frequency signal.

22. The bearing system of claim 21, wherein the modulated radio frequency signal generated by the radio frequency signal generator is an amplitude modulated radio frequency signal.

* * * * *